United States Patent
Aquino Olivos et al.

(10) Patent No.: US 9,791,359 B2
(45) Date of Patent: *Oct. 17, 2017

(54) PROCESS FOR DETERMINING THE INCOMPATIBILITY OF MIXTURES CONTAINING HEAVY AND LIGHT CRUDES

(71) Applicant: INSTITUTO MEXICANO DEL PETROLEO, Mexico City (MX)

(72) Inventors: Marco Antonio Aquino Olivos, Mexico City (MX); Adriana de Jesus Aguirre Gutierrez, Mexico City (MX); Jose Luis Mendoza De La Cruz, Mexico City (MX); Blanca Estela Garcia Flores, Mexico City (MX); Jacinto Aguila Hernandez, Mexico City (MX); Veronica Ramos Corzo, Mexico City (MX); Juan Carlos Cedillo Ramirez, Mexico City (MX); Oscar Alejandro Zamarripa Jimenez, Mexico City (MX)

(73) Assignee: INSTITUTO MEXICAN DEL PETROLEO, Mexico City (MX)

( * ) Notice: Subject to any disclaimer, the term of this patent is extended or adjusted under 35 U.S.C. 154(b) by 256 days.

This patent is subject to a terminal disclaimer.

(21) Appl. No.: 14/560,520

(22) Filed: Dec. 4, 2014

(65) Prior Publication Data

US 2015/0160110 A1    Jun. 11, 2015

(30) Foreign Application Priority Data

Dec. 6, 2013    (MX) .................... MX/a/2013/014349
Dec. 6, 2013    (MX) .................... MX/a/2013/014351

(51) Int. Cl.
| | | |
|---|---|---|
| G01N 9/02 | (2006.01) |
| G01N 9/36 | (2006.01) |
| G01N 11/14 | (2006.01) |
| G01N 33/28 | (2006.01) |
| G01N 9/00 | (2006.01) |

(52) U.S. Cl.
CPC ............... *G01N 9/36* (2013.01); *G01N 9/002* (2013.01); *G01N 11/14* (2013.01); *G01N 33/2823* (2013.01); *G01N 33/2835* (2013.01)

(58) Field of Classification Search
CPC ........................................................ G01N 9/36
See application file for complete search history.

(56) References Cited

U.S. PATENT DOCUMENTS

| | | |
|---|---|---|
| 4,627,272 A | 12/1986 | Wright |
| 4,853,337 A | 8/1989 | Dickakian |
| 4,864,849 A | 9/1989 | Wright |
| 5,025,656 A | 6/1991 | Wright |
| 5,871,634 A | 2/1999 | Wiehe et al. |
| 5,997,723 A | 12/1999 | Wiehe et al. |
| 6,584,831 B1 | 7/2003 | Kasameyer et al. |
| 7,029,570 B2 | 4/2006 | Mason et al. |
| 7,618,822 B2 | 11/2009 | Nemana et al. |

(Continued)

*Primary Examiner* — Clayton E Laballe
*Assistant Examiner* — Dennis Hancock
(74) *Attorney, Agent, or Firm* — Dickinson Wright PLLC

(57) ABSTRACT

A process for determining the incompatibility of crude mixtures (heavy, light) is based on the measurement of dynamic viscosity of crude mixtures using an electromagnetic viscometer having a mobile element (piston) move through the fluid to be measured at a constant force.

2 Claims, 4 Drawing Sheets

(56) References Cited

U.S. PATENT DOCUMENTS

2010/0069482 A1\* 3/2010 Longo ................ A61K 9/0048
 514/458
2016/0097757 A1\* 4/2016 Sieben .................... G01N 1/28
 436/60

\* cited by examiner

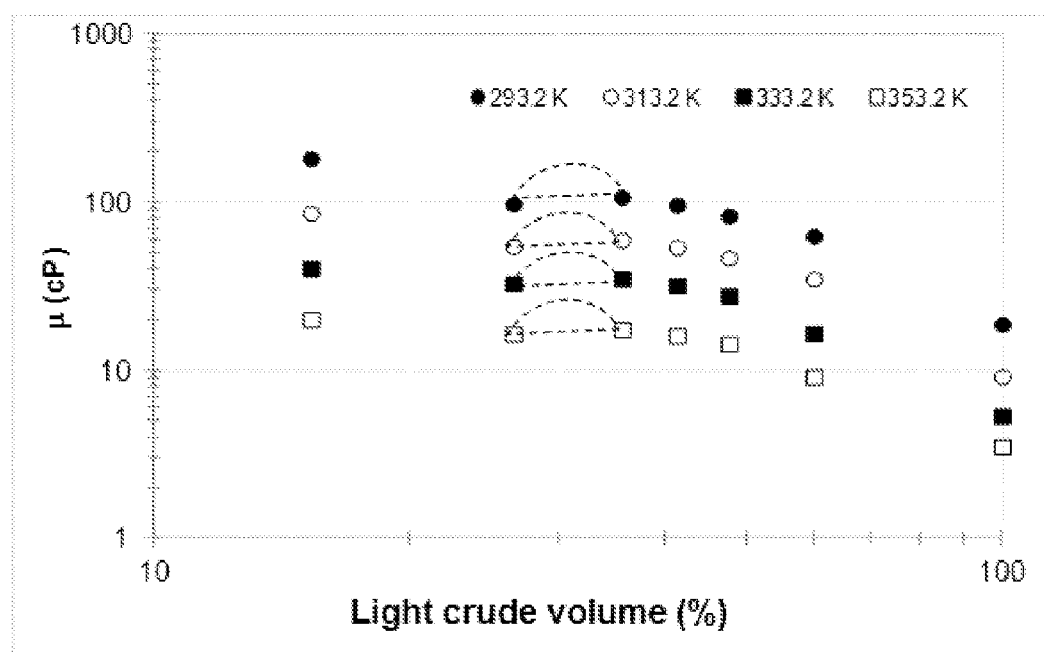

PROCESS FOR DETERMINING THE INCOMPATIBILITY OF MIXTURES CONTAINING HEAVY AND LIGHT CRUDES

CROSS-REFERENCE TO RELATED APPLICATIONS

This application claims the benefit and priority under 35 U.S.C. §119 to Mexican Patent Application No. MX/a/2013/014349 with a filing date of Dec. 6, 2013, and Mexican Patent Application No. MX/a/2013/014351 with a filing date of Dec. 6, 2013, the disclosures of which are incorporated herein by reference in their entirety.

Reference is hereby made to copending U.S. application Ser. No. 14/560,483 to Marco Antonio AQUINO OLIVOS et al filed Dec. 4, 2014, the disclosure of which is hereby incorporated by reference in its entirety.

FIELD OF THE INVENTION

This invention relates to a process for determining the incompatibility of a mixture of asphaltene-containing heavy and light crudes. More particularly, this invention is a process for determining incompatibility of an asphaltene-containing crude mixture based on measurement of dynamic viscosity.

BACKGROUND OF THE INVENTION

The study of petroleum analysis and its products would not be complete without considering the incompatibility that generates changes in its original properties. During and after the blending process, various secondary products can be formed such as sludge, semi-solids or solid particles increasing mixture viscosity. The term incompatibility refers to the formation of a precipitate (sludge, sediment and deposition of material with asphaltene content) or separation of phases when two liquids are blended (Speight 1999, 2004).

The phenomenon of incompatibility was firstly used by Martin (1951) defining it as the tendency of the fuel oil to produce a deposit in the dilution or blending with other fuel oils. Martin (1951) defined a difference between incompatibility and instability, as the tendency of a residual fuel to produce a deposit of asphaltic or carbonic material during storage or heating process. Instability during storage or during heating can be the result of the preparation of the fuel from incompatible components or can be the result of aging. The term instability is frequently used referring to color formation, sediment or bubble gum in the liquid during a period of time; this term can be used to differentiate the formation of a precipitate in short time (almost immediately). Nevertheless, the terms incompatibility and instability are used interchangeably (Speight, 1999).

The phenomena of incompatibility and instability of petroleum and its products are invariably associated with the chemical composition and physical ratio of the components. In the most of cases, a certain component in one the crudes reacts with another component in the crude with which is blended resulting in a chemical reaction in the formation of a new product that, when it is soluble, affects the mixture properties and when it is insoluble, it is deposited as a semisolid or solid matter (Speight, 1999). Normally, the incompatibility processes increase viscosity of petroleum and its derivatives, inclusively at low temperatures also causes a change in viscosity in certain fuels (Speight, 1999). Various studies demonstrated that blending of different crudes can lead to flocculation/precipitation of asphaltenes (Wiehe and Kennedy, 2000a, 2000b; van den Berg et al., 2003; Schermer et al., 2004). This phenomenon, known as crude incompatibility, causes problems in the transportation and refining process especially when the economical situation is requiring many refineries to carry out low cost crude blending to improve the refining margins (van den Berg et al., 2003).

Instead of various studies carried out in the last decades, there are always important questions in the chemistry and physics knowledge of the incompatibility phenomenon (Speight, 1999; Wiehe, 2012). It is well know that this problem did not lead to a standard method for determination and quantification of crude incompatibility. Based on the above, there are various criteria for determining crude incompatibility in literature.

U.S. Pat. No. 4,853,337 refers to a blending procedure of liquid hydrocarbons to control incompatibility mentioning that the paraffinic and condensed liquids can be blended with the crudes while the incompatibility of the asphaltenes is controlled; the incompatibility is expressed as the relation between the aromatics and the asphaltenes content of the crudes or liquid hydrocarbon.

Escobedo and Mansoori (1995) determine an incipient point in asphaltenes flocculation by means of relative viscosity measurement of a crude diluting it with a precipitating agent (n-pentane, n-heptane, n-nonane). The phenomenon is graphically shown with the increase of viscosity during the precipitation of the crude observing a deviation of the initial behavior during asphaltenes flocculation.

Asomaning (1997) shows the incompatibility phenomenon associating its solubility as the mechanism for deposits formation. Later, Asomaning and Watkinson (2000) introduced an index of simple colloidal instability (CII) based on the analysis of saturated, aromatic compositions, resins and asphaltenes (SARA) of the crudes mixture, concluding that mixtures with CII>1 tend to be incompatible and precipitate asphaltenes.

Buckley et al. (1998) associates the incipient point of precipitation to asphaltenes with solubility that depends on the refraction index (RI); in this work it is determined that the RI could be used to predict the incipient point of asphaltene precipitation. See also Buckley (1999) and Giménez and Cabeza (2006).

U.S. Pat. No. 5,871,634 refers to a method for blending two or more petroleum feedstreams, petroleum process streams or combination thereof, at least one of which includes the steps of determining the insolubility number, $(I_N)$ for each feedstream, determining the solubility blending number, $S_{BN}$, for each feedstream and combining the feedstreams in order of decreasing $S_{BN}$ number of each feedstream such that the solubility blending number of the mixture is greater than the insolubility number of any component of the mix, when the solubility blending number of any of the feedstreams or streams is equal or less than the insolubility number of any of the streams. See also the works of Wiehe and Kennedy (2000a, 2000b).

U.S. Pat. No. 5,997,723 refers to a process for blending crudes with the purpose of avoiding incrustation for crudes considered almost incompatible. See also the works of Wiehe et al. (2001) and Wiehe (2004).

Gharfeh et al. (2004) disclose an instrument for detection of diluted crudes incompatibility with heptane at low temperatures and atmospheric pressure. The measurement system consists in a titration container, an infrared laser and a detector for measuring light transmittance through the container. Initially, the transmittance increases and when it arrives to a flocculation point, it starts to decrease, then, the maximum point achieved is considered as the flocculation point of asphaltenes or the maximum dilution achieved.

U.S. Pat. No. 7,029,570 refers to a process for determining incompatibility in the crudes mixtures through the change in length density of neutrons dispersion at the surface of asphaltene aggregates.

U.S. Pat. No. 7,618,822 refers to crudes processing, mixtures and fraction in refines and petrochemical plants to decrease asphaltenes flocculation in the pre-heating train interchanger, ovens and other units of the refining process.

Flakier and Sandu (2010) disclose a technique for providing information on crudes stability on its mixtures detecting the incipient point of the asphaltenes flocculation based on very small changes of the composition of the mixtures using a source of transmission close to the infrared. The equipment used in this way has a detection system for solids able to measure the changes of intensity through the addition of a precipitate (n-pentane). An inflexion point of a transmittance graph based on the volume of precipitate added up to the start of flocculation can be observed. The inflexion point is expressed as the stability index of asphaltenes that corresponds to the precipitation point of asphaltenes and provides a relative measurement of the stability in the crude. Meanwhile, Sedghy and Goual (2010) determine the start of asphaltenes precipitation through the direct current conductivity technique in crudes diluted in toluene. Alvarez et al. (2012) use an ellipsometry technique to evaluate the compatibility of crudes mixtures.

Mexican Patent application No. MX/2011/003287, published Sep. 27, 2012 refers to a process for measuring dynamic viscosity of live heavy crude (monophasic samples taken from the well bottom) at a constant temperature and pressure from 68.9 MPa up to atmospheric pressure, including the dynamic viscosity in the bubble pressure point and under this least; that is, removing the gaseous phase and measuring liquid phase viscosity up to achieving atmospheric pressure.

Thus, an object of the present invention is to blend heavy and light crudes to decrease viscosity of the heavy crudes and to find the optimum concentration for maintaining asphaltenes below a predetermined level to reduce the tendency for asphaltene formation. According to the present invention, an incipient point of the asphaltene incompatibility threshold in the mixture is obtained that is a very important point to avoid because of the formation of asphaltene aggregates at a certain concentration of light crudes; the blending process comprises crudes with asphaltenes content.

The term "dead crude" as used in the present application is defined as a crude that has a sufficiently low pressure, does not contain dissolved gas or did not release its volatile components.

Similarly, the API gravity is a measure of density that describes how heavy or light the petroleum is compared with water. If the API gravity of the petroleum is more than 10, it is lighter than the water and therefore will float on it. The API gravity is also used to compare densities of fractions extracted from petroleum. For example, if a petroleum fraction floats on another; it means that it is lighter and therefore its API gravity is higher. Mathematically, the API gravity does not have units; nevertheless, this number always has the name API grade. The API gravity is measured with an instrument denominated densitometer; there are a great variety of these instruments. The °API of crudes oils, generally are in an interval of 47° (for lighter crudes) to 10° (for heavier crudes). Based on this parameter it is possible to classify the crudes in: extra heavy (°API<10), heavy (10.1<°API<22.3), mean or middle (22.4<°API<31.1), light (31.2<°API<38.9) and extra light (39.0<°API). It is important to mention that this classification can vary depending on the considered source.

The "room temperature" is the temperature where the laboratory is installed without having an external control of same, wherein any measurement is carried out, i.e. depending of the place where it can be found. For purposes of the description of the present invention, "room temperature" will be considered between 293.2 and 298.2 K.

Currently, there is no any reliable technique to determine the crude mixture incompatibility. Therefore, the present invention markedly overcomes prior techniques, since it provides the ratios of blending wherein the incompatibility of light and heavy crudes can occur through the determination of dynamic viscosity.

Therefore, another object of the present invention is to provide a process for measuring the dynamic viscosity of heavy and light crude mixtures with an apparatus containing a sensor based on a technique involving constant electromagnetic force.

Another object of the current invention is to provide a process for determining crude mixture incompatibility by measuring the dynamic viscosity of the mixtures at different temperature and pressure conditions.

SUMMARY OF THE INVENTION

A process has now been found for determining the incompatibility of an asphaltene-containing heavy crude in admixture with a light crude, which process comprises forming mixtures of heavy crude and light crude, and determining the incipient point of asphaltene incompatibility by dynamic viscosity measurement of the mixtures at varying concentrations of light crude.

According to a preferred embodiment of the invention, the incipient point of asphaltene incompatibility is determined with an apparatus involving a piston-type member, calibrated in a determined interval of viscosities, that is submerged in a crude mixture. The piston displacement is hampered by the viscous pull of the crude fluid, a characteristic that is used to obtain an exact measurement of absolute viscosity. The time required for the piston to go over a given distance is related to the dynamic viscosity of the fluid confined in a measurement chamber, therefore, as the fluid in the chamber is more viscous, the piston displacement will be slower.

According to another embodiment of the invention, the process for determining incompatibility of heavy and light crude comprises the following steps:

A: preparing mixtures of heavy and light crudes comprising 0%, 25-35%, 40-50%, 60-75% and 100% by volume of light crude;

B: loading a heavy and light crude mixture to a high-pressure stainless steel container (up to 68.9 MPa) for connecting the circuit of measurement apparatus for measuring dynamic viscosities;

C: adjusting the temperature in the system through the recirculating bath (up to 463 K) for an isothermal and isobaric transfer;

D: stabilizing the system to constant temperature in the range of 463 K to room temperature and a pressure of from 0.1 to 68.9 MPa to register dynamic viscosity values $\mu_{od}$ and measuring temperature for subsequently increasing the temperature in the system by means of a recirculating bath until the analysis temperature is newly established, the viscosity value for the temperature is registered at a constant pressure of 0.1 to 68.9 MPa, and immediately repeating step D up to a selected temperature;

E: monitoring the viscosity behavior of the sample based in the light crude added to a constant temperature for experimental determination of the incipient point of asphaltene incompatibility threshold in the crudes mixtures through the viscosity behavior of the mixture based on the light crude added to a constant temperature;

F: preparing mixtures of heavy crude with light crude with percentages of light crude volume less than the inflexion point found in step E and repeating Steps B, C, D and E when the viscosity behavior vs. volume percentage added of light crude, is not the typical behavior;

G: repeating step F until the slope change in the viscosity behavior of dynamic viscosity of the mixture corresponds to the minimum percentage of light crude added.

According to another embodiment of the invention, the measurement apparatus for measuring dynamic viscosities comprises (i) a piston containing a ferromagnetic material; (ii) a piston guide that leads it along an established pathway; (iii) two electromagnetic coils placed in the measurement chamber to produce respective magnetic fields that lead the piston all along its path in respective opposite directions and (iv) a detector of position sensitive to inductance of the coils to produce an indicative detection signal that the piston has reached voyage extreme positions.

BRIEF DESCRIPTION OF THE DRAWINGS

FIG. 7 shows (in logarithmic scale) dynamic viscosities of the mixtures {light crude+heavy crude} vs. volume percentage of light crude added, at different temperatures and pressure of 0.1 MPa.

DETAILED DESCRIPTION OF THE INVENTION

Figure 1:
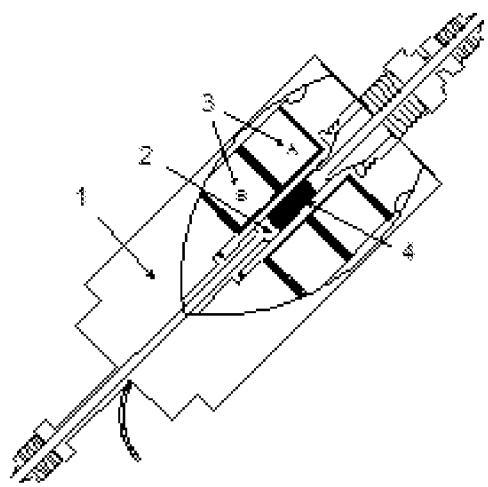
FIG. 1 shows an electromagnetic viscometer 1 in partial cross-section used in the present invention.

The current invention refers to a process based on the measurement of dynamic viscosities of crudes mixtures using a constant force electromagnetic viscometer to determine the incompatibility of heavy and light crudes in the interval of temperature of 463 K at room temperature and pressures of 0.1 to 68.9 MPa. Blending comprises crudes with asphaltene content. The blending process included a procedure to determine the incipient point of the asphaltenes incompatibility threshold in the mixture. The apparatus used in the current invention is simple from a mechanical point of view and the principle basis for determining that viscosity is effective (See U.S. Pat. No. 6,584,831; U.S. Pat. No. 5,025, 656, U.S. Pat. No. 4,864,849, U.S. Pat. No. 4,627,272, MX/2011/003287A, the disclosures of which are herein incorporated by reference in their entireties). The apparatus is precise, reliable, and easy to use and with maintenance without any difficulty. It is based on a simple electromagnetic and reliable principle that uses only a mobile element (piston containing ferromagnetic material), at a constant force, submerged in the fluid to be analyzed. The time required for the piston to travel a given distance is directly related to the dynamic viscosity of the fluid confined in a measurement chamber (FIG. 1). The object of this invention is to measure the viscosity of a heavy crude diluted with a precipitating agent to precisely know which concentration of precipitating agent results in the asphaltenes formation known as the incipient point or star of the asphaltenes precipitation to avoid formation or aggregation of asphaltenes in an industrial application or process in the field. By determining the incipient point of asphaltene incompatibility, one can add a predetermined volume of light crude below such incipient point to the heavy crude/light crude mixture to provide desired pumpability and/or storability of the heavy crude/light crude mixture without encountering aggregation and precipitation of the asphaltenes that cause pipe blockage and other related problems.

The present process involves a mixture of asphaltene-containing heavy and light crude oils. The present process can be used to determine the incipient point of an asphaltene-containing hydrocarbon mixture or blend, preferably involving heavy crude and a lighter hydrocarbon. Preferably, the present process is applicable to an asphaltene-containing mixture or blend of a heavy crude with a lighter hydrocarbon, and more preferably a light crude oil that when mixed or blended with a heavy crude can result in the precipitation of asphaltenes from the mixture or blend at a particular volume % of the light hydrocarbon or light crude. Thus, the term light crude as used can be any hydrocarbon fraction having an API gravity greater than 20 or greater than 30, preferably between 31 and 42, or more preferably between 31.2 and 38.9. FIG. 1 shows a cross section of the electromagnetic viscometer 1 used in the current invention. The apparatus comprises a measurement chamber 1 where piston 4 is located and travels forward and back alternatively driven by electromagnetic coils 3 (A and B). One of the coils is located such that when the current flows through it, the resulting magnetic field tends to drag the piston in one direction along the channel. The second coil is placed such that the resulting magnetic field forces the coil along the channel in an opposite direction.

The alternative conduction of the two electromagnetic coils with its particular conduction device and sensitive to the position detector that changes between the two electromagnetic coils. as well as the adjustment of the duration of the time interval predetermined used during the distance (traveled by the piston) of the conduction to a determined value based on the duration of at least a previous travel of the piston.

The response to the first travel of the piston to the end of a time interval (maintaining the duration of the time interval to a fixed value) for a period comprising a plurality of travels of the piston at least of the detection signal does not indicate that the piston has reached one of the final positions of the voyage.

The adjustment of the time duration predetermined for the first travel of the piston after the emptying period of values to a value of at least six times the emptying value; as well as the response to the duration of conduction travel.

The apparatus of the present invention preferably comprises the following peripherals: (i) a pressure transducer and its digital indicator, (ii) a recirculating bath, (iii) high-pressure stainless steel containers including stainless steel floating pistons, (iv) high-pressure stainless steel pipelines of ⅛" internal diameter, (v) high-pressure stainless steel valves to control the flow of crudes mixture, (VI) a computer for registering and storing the data, (vii) a positive displacement pump to generate and control pressure in the system, (viii) pressurization fluid, (xi) a temperature gauge welded at the bottom of the body to the measurement apparatus, (x) a vacuum pump, (xi) a plastic pipeline of ⅛" internal diameter, (xii) heating or insulating tapes, (xiii) temperature controllers.

The present method is based, for example, on viscosity measurements of a crude that is diluted with a precipitating agent (i.e. n-pentane, n-heptane, etc.) at a defined concentration (interval of 0.01 to 99.9% by volume), with a volume of 25 mL of sample, viscosities in the interval of 0.2 to 10000 cP, at a temperature up to 463 K and pressures of 0.1 to 68.9 MPa. The incipient point of flocculation/precipitation of asphaltenes is detected when there is an unusual increase of viscosity (relative) of the suspension where the asphaltene particles aggregation occurs.

Figure 4:
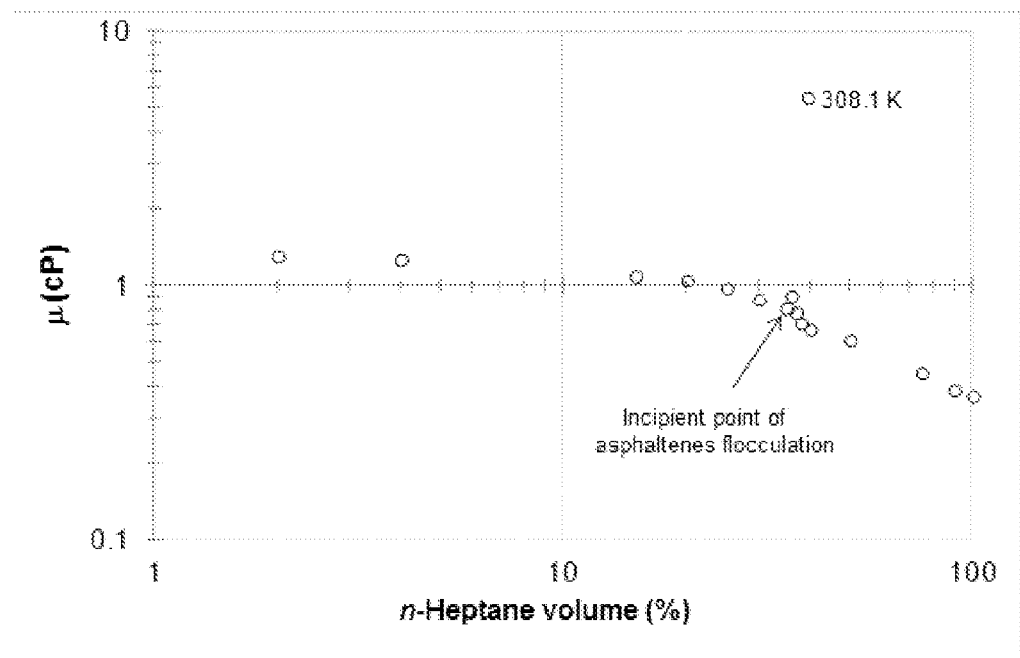
FIG. 4 refers to the results of dynamic viscosity obtained for the mixture {light crude–toluene+n-heptane} (in logarithmic coordinates)

FIG. 4 shows the effect of adding n-heptane in excess at a constant temperature and 0.1 MPa. In literature, this behavior of slope change or inflexion point in the viscosity based on the volume % of precipitating agent is referred to as the incipient point of asphaltenes flocculation. It can be observed in FIG. 4 that the behavior of the mixture dynamic viscosity {light crude-toluene+n-heptane} shows (in logarithmic scale) a decrease when it is added to the precipitating agent; the value of viscosity has a minimum value for precipitate volume fraction in the interval of 2-35%, After this minimum value, the dynamic viscosity of the mixture increases in the flocculation/precipitation threshold up to obtaining a maximum value in this region. Adding n-heptane in excess at a constant temperature and 0.1 MPa. In literature, this behavior of slope change or inflexion point in the viscosity based on the volume % of precipitating agent refers to, as the incipient point of asphaltenes flocculation Based on the above description, it can be concluded that the incipient point of flocculation/precipitation of asphaltenes corresponds to the immediately previous point when viscosity increases, that is, the 35% by volume of n-heptane in the mixture.

Figure 5:
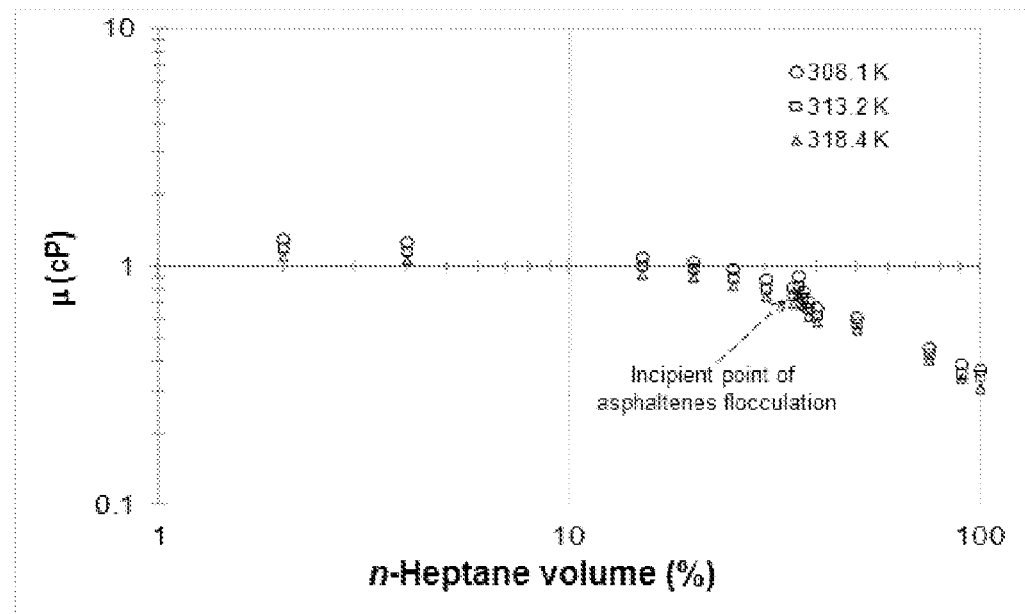
FIG. 5 shows (in logarithmic coordinates) three slopes of dynamic viscosity (at temperatures of 308.1 K, 313.2 K and 318.4 K and a constant pressure of 0.1 MPa) for the system {light crude–toluene+n-heptane}.

It can be observed in FIG. 5 that the incipient point of asphaltenes flocculation/precipitation coincides in the same relation (35% by volume) of n-heptane in the mixture at three different temperatures, i.e. 308.1 K, 313.2 K and 318.4 K and a constant pressure of 0.1 MPa.

Figure 6:
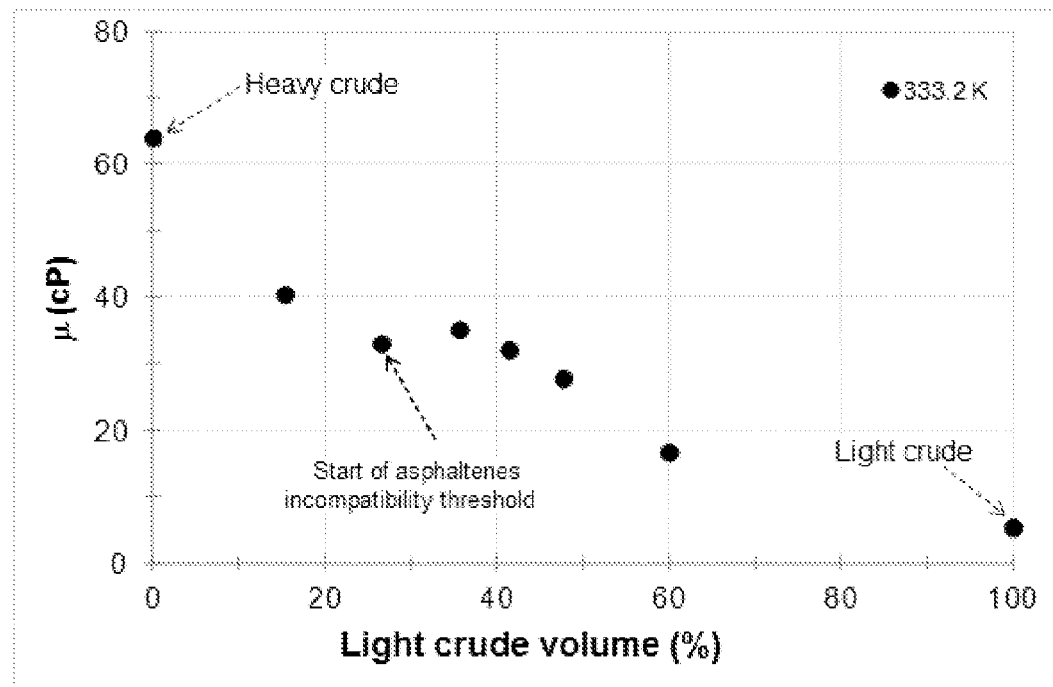
FIG. 6 shows the results obtained from viscosities of a heavy and light crude mixture (including viscosities of heavy and light crude)

FIG. 6 shows the dynamic viscosities measured at 333. K in various mixtures {light crude+heavy crude} between 0 and 100% by volume of light crude at 332.2K and pressure of 0.1 MPa. At low volume fractions of the added light crude (up to ~15%), viscosity gradually decreases and then has a considerable increase of viscosity when the volume fractions of light crude exceed 26.6; this increase of viscosity achieves a maximum value and then the viscosity of the mixture gradually decreases.

Based on the previously described criteria, the incipient point of asphaltenes flocculation/precipitation or the incipient point of flocculation threshold (or in this case, the incipient point of asphaltenes incompatibility threshold) was determined to be 26.6 volume % of light crude in the light crude/heavy crude mixture.

It can be seen in FIG. 7 (in logarithmic scale) that the dynamic viscosity slopes vs. volume percent of light crudes showed the same behavior at different temperatures, that is, firstly a decrease of viscosity until obtaining a minimum value afterwards an important increase in the asphaltenes incompatibility threshold. This figure shows the incipient point of the asphaltene incompatibility measured or mixtures of these two crudes (heavy and light) at four different temperatures and 0.1 MPa. In the temperature range of 293.2-353.2 K, the incipient point starts when the fraction of light crude in the mixture is of 26.7%. The shadowed area in FIG. 7 shows the incompatibility threshold for each temperature.

It is evident that the asphaltenes are maintained in the crude in a delicate balance (Speight, 1999) and this balance can be easily disturbed by the addition of saturated and removal of resins and aromatic (Wiehe and Kennedy, 2000b; Wiehe, 2012); therefore, the crudes blending can greatly change the global concentration of these molecular types altering this balance and flocculation/precipitating the asphaltenes.

The following example is illustrative only, and is not intended to limit the claimed invention.

Example

In order to guarantee that determination of dynamic viscosities are reliable, the piston to be used, pressure transducer and system temperature gauge were previously calibrated. The calibration and verification of the piston was carried out with S20, N4, S6 standards) provided by Cannon Instrument Company, ASTM S2162) and involves the measurement of a standard fluid that can be identified at a stable temperature and that adjust the calibration parameters related to the selected piston to reproduce dynamic viscosity (with a mean absolute deviation of ±1.0%) corresponding to the known value of said calibration standards to the established temperature.

Figure 2:
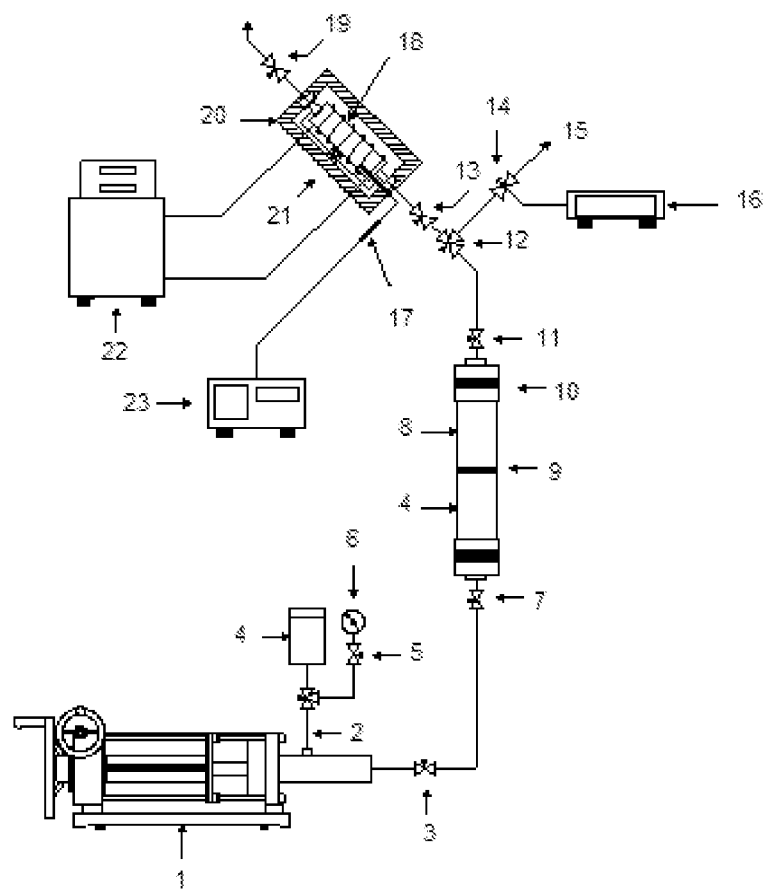
FIG. 2 shows a schematic diagram for measurement of dynamic viscosity of reservoir fluids.

The following examples show the operation of the process and apparatus described herein to determine the incompatibility in the crudes blending (heavy, light) in an interval of temperature of 463 K and room temperature and pressure of 0.1 MPa (See FIG. 2). A similar system is described in the doctoral thesis entitled "DETERMINACIÓN EXPERIMENTAL DE LA INCOMPATIBILIDAD/COMPATIBILIDAD DE MEZCLAS DE HIDROCARBUROS MEDIANTES LAS TÉCNICAS DE VISCOMETRÍA Y DENSIMETRÍA", 77 pages, Escuela Superior de Ingeniería Química e Industrias Extractivas, Instituto Politécnico Nacional by Juan Carlos CEDILLO RAMÍREZ, Published on Jan. 28, 2013, the disclosure of which is hereby incorporated by reference in its entirety.

FIG. 2 shows a schematic diagram for measurement of dynamic viscosity of reservoir fluids. A small volume quantity of sample contained in the high-pressure stainless steel container is requested to carry out viscosity measurement at different temperature and pressure conditions. The temperature inside the measurement chamber is measured with a temperature gauge 17 connected to a digital indicator 23. A pressure transducer together with a digital indicator 16 is connected to viscometer 18 to monitor the pressure in the measurement system. A serial interface RS-232 allows the communication of viscometer 18 with a computer. In order to generate pressure in the system, a positive displacement pump 1 is used, meanwhile for temperature generation in the apparatus; a recirculating bath 22 is used (MX/2011/003287A).

Step A.

Mixtures of heavy and light crudes of 0%, 25-35%, 40-50%, 60-75% and 100% by volume of light crude were prepared.

Step B.

The heavy and light crude mixture 1 is loaded in a high-pressure stainless steel container 10 and connected to the measurement circuit through the valves 7 and 11. The high-pressure stainless steel container 10 contains a high-pressure stainless steel piston 9 inside that freely floats through the stainless steel container 10 separating the mixture 8 of the pressurization fluid 4. In order to maintain a homogeneous temperature in the measuring system, the high-pressure stainless steel container 10 is heated with a heating resistance. The stainless steel pipelines that integrate the measuring circuit are also heated with heating tapes.

Step C.

The temperature in the system is established through the recirculating bath 22. The temperature in the apparatus is measured by a temperature detector 17 that is connected to a digital indicator 23. The pressure in the system is generated and controlled by a positive displacement pump 1 that used a mineral oil 4 as pressurization fluid. The pressure in the system is monitored by a pressure transducer connected to pressure digital indicator 16. When the temperature in the apparatus 18 is close to the measurement temperature, the apparatus 18 is vertically placed and is connected to a vacuum pump 15 by the valve 14. The valves 12, 13, 14 and 21 must be open during the vacuum process; meanwhile the valves 11 and 19 must be maintained closed. The measuring circuit is emptied up to obtaining an appropriate vacuum (generally, after 20 minutes approximately), close the valves 14, 12, 13 and 21. Establish the required pressure in the positive displacement pump 1 and open slowly the valves 3, 7, 11, 12, 13 and 21. The valve 2 must be maintained closed; meanwhile the valve 5 must be open. In order to ensure that the system was filled with the mixture, purge a small volume quantity for the valves 14 and 19. Close slowly the valve 21 and place the apparatus 20 in measuring position (45° C.).

Step D.

When the mixture is stabilized at a temperature and pressure of 0.1 MPa, the values of dynamic viscosity and measuring temperature were recorded. Afterwards, temperature in the system is increased through a recirculating bath 22; when the analysis temperature is newly stabilized, the viscosity values for temperature and pressure of 0.1 MPa are registered. Repeat Step D up to the temperature of 463 K or any other temperature.

Step E.

Monitor the behavior of the mixture viscosity based on the light crude added at a constant temperature for experimental determination of the incipient point of asphaltenes incompatibility threshold in crudes mixture through the mixture viscosity behavior based on the light crude added at a constant temperature; i.e. through the graphic observation of the slope change of behavior vs. light crude added (%).

Step F.

Figure 3:
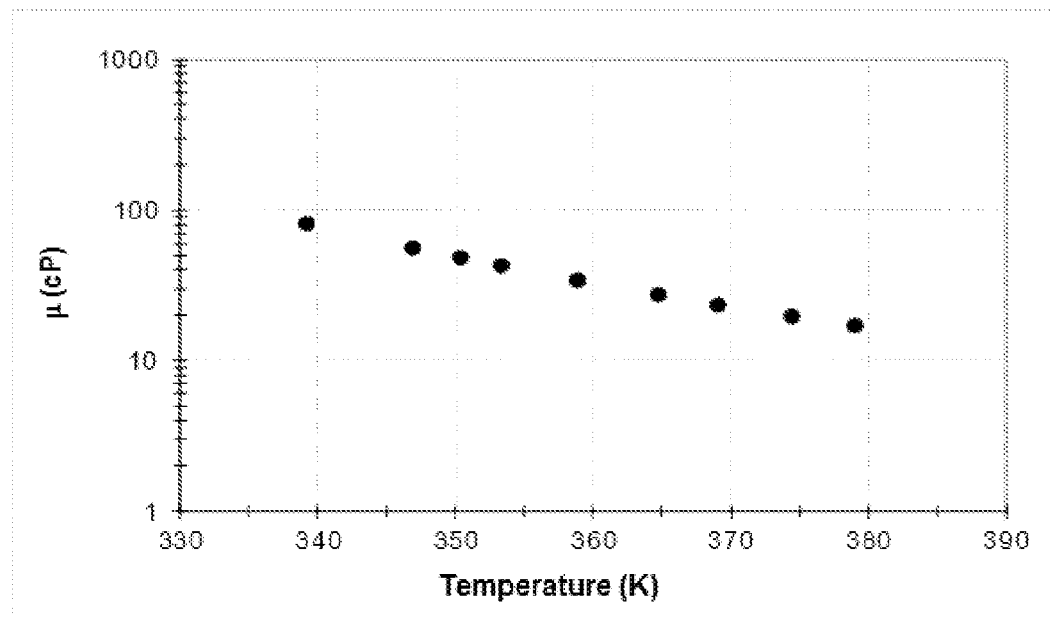
FIG. 3 shows the typical behavior (in logarithmic coordinates in the Y-axis) of the viscosity of a dead crude based on constant temperature and pressure.

The typical behavior of a dead crude is shown in FIG. 3, namely, the viscosity decreases when the temperature increases. Generally, the laboratory studies measure the behavior of the dead crude viscosity based on the room temperature up to the reservoir temperature;

If the behavior of the viscosity vs. percentage by volume added of light crude, is not the typical behavior shown in FIG. 3, mixtures of heavy and light crudes are prepared with volume percentages of light crude less than the inflexion point found in Step E and steps B, C, D and E are repeated.

Step G.

Step F is repeated until the slope change in the dynamic viscosity behavior of the mixture corresponds to the minimum percentage of added light crude (as observed in FIG. 6); the immediately previous point to the slope change (or inflexion point) of viscosity is considered as the incipient point of the asphaltenes incompatibility threshold.

It is well known that the asphaltenes is a crude fraction that can be precipitated when it is blended with non-polar hydrocarbon (n-pentane, n-heptane) or when two or more crudes are blended, tamponades or blockages are caused in the pipelines, tanks, heat interchanger, etc.

The present invention consists of determining the concentration when the precipitation starts, that is, when they are incompatible. The incompatibility can be determined from the viscosity measurement based on the concentration, at a given temperature.

The viscosity results shown in FIG. 6 clearly indicate where incompatibility occurs in a mixture of heavy and light crude showing the inflexion point in the graphic. It is important to have an adequate mixing due to the fact that small quantities of flocculated material loose energy due to little transfer of heat. Moderate quantities of asphaltenes cause pressure drops and interfere in the equipment operation, resulting in an inefficient process. Finally, large quantities of asphaltenes cause intolerable blockages or tamponades and cause the process to stop until the pipelines are cleaned. That is why it is important to find the incompatibility point (the optimum mixture) to avoid the above-mentioned problems.

What is claimed is:

1. A process for determining the incompatibility of an asphaltene-containing mixture of heavy crude and light crude and preparing a heavy crude/light crude mixture without aggregation and precipitation of asphaltenes, said process comprising: forming a plurality of sample mixtures of heavy crude and different amounts of light crude containing asphaltenes, determining the incipient point of asphaltene incompatibility by dynamic viscosity measurements of each of the sample mixtures at the different concentrations of light crude, and adding a volume of light crude to a mixture of the heavy crude and light crude mixture in an amount below the incipient point of said heavy crude and light crude mixture without causing aggregation and precipitation of asphaltenes from said mixture, where the amount of light crude added is based on the measurement of the incipient point of asphaltene incompatibility of each of said plurality of sample mixtures.

2. A process for determining incompatibility of heavy and light crude and preparing a heavy crude/light crude mixture without precipitation of asphaltenes, comprising the following steps:

A: preparing a plurality of sample mixtures of heavy and light crudes comprising 25-35%, 40-50%, and 60-75% by volume of light crude;

B: loading each heavy and light crude sample mixture to a high-pressure stainless steel container (up to 68.9 MPa) for connecting the circuit of measurement apparatus for measuring dynamic viscosities;

C: adjusting the temperature in the system through the recirculating bath (up to 463 K) for an isothermal and isobaric transfer;

D: stabilizing the system to constant temperature in the range of 463 K to room temperature and a pressure of from 0.1 to 68.9 MPa and measuring dynamic viscosity values $\mu_{od}$ and measuring temperature for subsequently increasing the temperature in the system by means of a recirculating bath until an analysis temperature is newly established, the viscosity value for the temperature is registered at a constant pressure of 0.1 to 68.9 MPa, and immediately repeating step D up to a selected temperature;

E: monitoring the viscosity behavior of each sample mixture based on the amount of light crude in the sample mixture to a constant temperature for experimental determination of the incipient point of asphaltene incompatibility threshold in the crude sample mixtures through the viscosity behavior of the mixture based on the light crude in the sample mixture to a constant temperature;

F: preparing sample mixtures of heavy crude with light crude with percentages of light crude volume less than an inflexion point found in step E and repeating Steps B, C, D and E when the viscosity behavior vs. volume percentage added of light crude, is not typical behavior;

G: repeating step F until a slope change in viscosity behavior of dynamic viscosity of the mixture corresponds to the minimum percentage of light crude added to determine the incipient point of asphaltene precipitation, and adding a light crude to a heavy crude/light crude mixture in an amount below the incipient point to prevent asphaltene precipitation.

* * * * *